United States Patent [19]  [11] 3,979,471
Julia  [45] Sept. 7, 1976

[54] PROCESS FOR SYNTHESIZING ETHYLENIC COMPOUNDS

[75] Inventor: Marc Julia, Paris, France

[73] Assignee: Agence Nationale de Valorisation de la Recherche (ANVAR), Neuilly-sur-Seine, France

[22] Filed: Aug. 2, 1974

[21] Appl. No.: 494,430

[30] Foreign Application Priority Data
Aug. 10, 1973 France .............................. 73.29329

[52] U.S. Cl........................... 260/666 A; 260/456 P; 260/456 R; 260/488 B; 260/488 CD; 260/488 F; 260/607 A; 260/638 R; 260/669 QZ; 260/681; 260/682

[51] Int. Cl.$^2$........................ C07C 1/22; C07C 1/24

[58] Field of Search............ 260/682, 666 A, 668 R, 260/456 R, 456 P, 488 F, 488 CD, 681, 669 QZ

[56] References Cited
UNITED STATES PATENTS
3,830,862   8/1974   Meyers et al. ...................... 260/682

OTHER PUBLICATIONS
Pascali et al., *J. Chem. Soc.*, Perkin I, 1166–1168 (1973).

Primary Examiner—D. Horwitz
Attorney, Agent, or Firm—Alan H. Levine

[57] ABSTRACT

The invention relates to a process for the preparation of ethylenic compounds and to certain novel ethylenic compounds produced by the process.

The process comprises the reaction of an appropriate carbonyl compound with a sulphone to obtain an alcohol sulphone which is then reduced to obtain the desired ethylenic compound.

11 Claims, No Drawings

PROCESS FOR SYNTHESIZING ETHYLENIC COMPOUNDS

This invention relates to a new process for synthesising ethylenic compounds from aldehydes or ketones and sulphones.

BACKGROUND OF INVENTION

The most widely known process in current use for the production of ethylenic compounds from aldehydes or ketones comprises reacting these carbonyl compounds with a phosphonium halide, for example triphenyl alkyl phosphonium bromide which itself is obtained by reacting triphenylphosphine with an alkyl bromide. Although this reaction takes place satisfactorily, the starting triphenylphosphine is converted into triphenylphosphine oxide which has to be reduced for recycling. Another method of synthesising ethylenic compounds from aldehydes or ketones comprises reacting the aldehydes or ketones with sulphone, for example with phenyl benzyl sulphone, to form an alcohol sulphone (*Journal of Chemical Society* PERKIN I, page 1166, 1973) which is then converted into an ethylenic sulphone by treatment with a dehydrating agent such as phosphoric acid. The treatment of this sulphone with a reducing agent, such as aluminium amalgam or a metal hydride, results in splitting of the sulphonyl group and liberates the required ethylenic compound (*Journal Chemical Communications*, page 351, 1973). The advantage of this method, in which hydroxysulphones are formed as intermediate stage, is that it gives high yields, but unfortunately the successive stages of dehydration and desulphonation each necessitate a different agent and, on completion of dehydration, the ethylenic sulphone obtained has to be dehydrated in order to be able to subject it to the reducing splitting treatment.

SUMMARY OF INVENTION

The present invention relates to a simpler process for the preparation of ethylenic compounds corresponding to the formula:

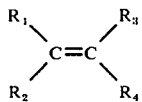

in which $R_1$ and $R_3$, which may be the same or different, represent a hydrogen atom or a methyl radical, $R_2$ represents a hydrogen atom, a saturated or unsaturated, linear or branched aromatic or aliphatic radical, and $R_4$ represents a saturated or unsaturated, linear or branched ethylenic or polyenic aliphatic radical, the radicals $R_3$ and $R_4$ being attachable to one another to form a ring with the ethylenic carbon, wherein an aldehyde or ketone of the formula $R_3 - CO - R_4$ is reacted with a sulphone of the formula $R_1 - CH(R_2) SO_2R$, in which R represents an alkyl, aryl or cycloalkyl radical, in the presence of a basic agent, and the product obtained treated with a reducing agent.

The process according to the invention comprising these two stages of preparation can be represented by the following reaction scheme:

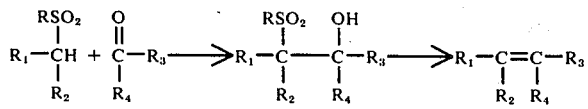

In one advantageous variation, the alcohol sulphone its esterified before treatment with the reducing agent. In this way, it is possible to convert the alcohol sulphone into its mesylic or tosylic or even carboxylic esters, such as for example its acetic ester, by the methods normally used for esterifying alcohols.

The starting sulphones are known products such as, for example, methylphenyl sulphone, ethylphenyl sulphone, isopropylphenyl sulphone, dimethylsulphone. They can also be new products prepared by conventional methods, in particular by reacting an alkaline sulphinate with a monohalogenated derivative, for example with an alkyl halide.

The aldehydes and ketones used are known, optionally saturated aliphatic or aromatic products such as acetone, methylethyl ketone, diethyl ketone, methylvinyl ketone, 6-methyl-2-heptenone, cyclohexanone, acetophenone, benzophenone, acetaldehyde, propionic aldehyde, valeric aldehyde, benzaldehyde, cinnamic aldehyde and their homolognes, acrolein, methacrolein, crotonaldehyde, senecioic aldehyde, citral, vitamin A aldehyde, and apocarotenals.

In the first stage of the process, condensation of the sulphone with the carbonyl compound is carried out by keeping these products in contact in a molar ratio of 1:1 in the presence of a basic agent sufficiently active to anionise the sulphone used. This alkaline agent can be selected from the oxides or hydroxides of alkali metals, the hydrides, amides or alcoholates of alkali metals.

It is also possible to use an active metallation agent, such as an organomagnesium, organolithium or organozinc compound. The quantity of alkaline agent can be varied from 1 to 1.2 mol per mol of sulphone. In general, a molar ratio of 1:1 is perfectly suitable.

The reaction can be carried out either at ambient temperature or at lower temperatures down to −80°C, and preferably in a solvent which is inert under the reaction conditions, such as an aliphatic or aromatic hydrocarbon, an alcohol, an ether or a polar solvent.

The first stage of the process yields an alcohol sulphone.

Of the alcohol sulphones that have been prepared, some are already known, whilst others are new products which, independently of the present process, can be used for other organic syntheses, for example in the preparation of α,β-ethylenic sulphones, known more commonly as vinyl sulphones.

To carry out the second stage of the process, the alcohol sulphone may optionally be esterified as indicated above before being treated with a reducing agent.

Reducing agents particularly suitable for converting the alcohol sulphone into an ethylenic compound are amalgams of alkali metals, such as sodium or potassium amalgam. The amalgam is used in such a quantity that the reaction mass contains a molar quantity of alkali metal equal to or greater than that of the alcohol sulphone. The reaction can be carried out at ambient temperature or at lower temperatures down to −50°C. It is carried out in a solvent such as an aliphatic or aromatic hydrocarbon, an alcohol, a linear or cyclic ether.

The ethylenic compound is isolated from the reaction mixture by extraction with a solvent, by distillation or by any other known method.

A sulphinic derivative, for example an alkali phenyl sulphinate, is formed as secondary product during the second stage of the process, and can be reused in the preparation of the starting sulphone.

DESCRIPTION OF PREFERRED EMBODIMENTS

The process according to the invention is illustrated by the following Examples.

EXAMPLE 1

In a flask filled with nitrogen, 1.56 g ($10^{-2}$ mols) of phenylmethyl sulphone were dissolved in 20 cc of tetrahydrofuran previously distilled in a nitrogen atmosphere. The temperature was then reduced to −78°C, followed by the addition over a period of 2 minutes of 0.64 g ($10^{-2}$ mols) of butyl lithium in solution in hexane. White crystals of lithium-containing phenylmethyl sulphone formed after 3 to 5 minutes, the temperature was allowed to rise to 0° − 10°C. The temperature was then reduced to −30°C to −40°C, followed by the rapid addition of 1.06 g ($10^{-2}$ mol) of freshly distilled benzaldehyde in solution in 5 cc of tetrahydrofuran. The lithium-containing phenylmethyl sulphone precipitate disappeared and the solution was stirred for 1 hour at −20° to −30°C. This was followed by the addition of 1.26 g (1.1 $10^{-2}$ mol) of methyl sulphonic acid chloride in 5 cc of tetrahydrofuran and 4 cc of hexamethyl phosphoramide. The reaction mixture was left standing overnight at −20° to −30°C. and was then hydrolysed with an aqueous saturated solution of ammonium chloride, followed by extraction 3 times with ether. The combined ethereal phases were washed with a saturated aqueous solution of sodium chloride. The ether was evaporated in the absence of heat, leaving 3.45 g of crystals deliquescing at ambient temperature which we stored below 0°C.

These crystals were identified by infrared spectrography as being 2-phenylsulphonyl-1-mesyloxy-1-phenyl ethane.

612 mg (1.8 . $10^{-3}$ mol) of the crystals previously obtained were dissolved in 6 cc of absolute methanol. The solution was stirred with a magnetic stirrer and its temperature reduced to −30°C. 4 g of sodium amalgam were then added overnight. The mixture was then decanted and the upper layer anionised by vapour-phase chromatography at 100°C, showing that 136 mg of styrene had been obtained without even the slightest trace of ethyl benzene.

EXAMPLE 2

Following the procedure of Example 1, the lithium-containing phenylmethyl sulphone was prepared from 1.56 g of phenylmethyl sulphone in hexane. After the temperature had been reduced to −40°C, 0.98 g ($10^{-2}$ mol) of cyclohexanone in 5 cc of tetrahydrofuran were added, followed by the addition at −25°C of 1.26 g of methyl sulphonic acid chloride in 5cc of tetrahydrofuran and 4 cc of hexamethyl phosphoramide. The reaction mixture was treated in the same way as in the preceding Example and 3.4 g of deliquescent crystals were isolated, being identified by infrared spectrography as 1-phenyl sulphonyl methyl-1-mesyloxy cyclohexane.

682 mg (2.08 . $10^{-3}$ mols) of the crystals previously obtained were dissolved in 6 cc of methanol. The solution was stirred at −30°C, followed by the addition of 4.2 g of 6% sodium amalgam. The mixture was then stirred overnight at −30°C. The decanted upper layer was found by chromatography to contain methylene cyclohexane identical with the product described in *Organic Syntheses*, Vol. 40, page 67. Yield: 85%.

EXAMPLE 3

8.5 g ($5.10^{-2}$ mols) of phenylethyl sulphone in 100 cc of benzene were added to $5.10^{-2}$ mols of ethyl magnesium bromide in 50 cc of ethyl ether at ambient temperature. The mixture was heated under reflux for 1 hour, and then cooled to ambient temperature. Following the addition of 4.8 g (5.25 $10^{-2}$ mols) of freshly distilled valeric aldehyde, the mixture was stirred overnight. The reaction mixture was then treated in the same way as in the preceding Examples, giving 13 g of a crude oil which by distillation in vacuo, gives a fraction of 8.5 g of a yellowish oil, b.p.$_{4.10}^{-3}$ = 187°− 189°C, which was identified by centesimal analysis and infrared spectrography as being 2-phenyl sulphonyl-3-hydroxy heptane which corresponds to the formula:

, $CH_3 — CH (SO_2C_6H_5) — CHOH — (CH_2)_3 — CH_3$

NMR analysis indicated the presence of two diastereo isomers in proportions of 50/50.

100 mg ($4.10^{-4}$ mols) of this product were dissolved in 3 cc of absolute methanol, 0.6 g of 6% sodium amalgam added and the mixture stirred overnight. The upper layer was then decanted and analysed by vapour-phase chromatography. It was found to contain a quantity of 2-heptene corresponding to a yield of 63%.

EXAMPLE 4

Following the procedure of Example 1, 0.850 g of phenylethyl sulphone and 0.430 g of valeric aldehyde were condensed with n-butyl lithium. Methyl sulphonic acid chloride was then added and, after standing overnight at −30°C, the reaction mixture was treated in the usual way, giving 1.72 g of a yellow oil which was 2-phenyl sulphonyl-3-mesyloxy heptane. 282 mg of this product in solution in methanol were then reduced by the addition of 1.5 g of 6 % sodium amalgam, followed by stirring overnight at −30°C. The upper decanted layer was analysed by vapour-phase chromatography. 2-Heptene was obtained in a yield of 80 % without any traces either of 1-heptene or of 3-heptene.

EXAMPLE 5

1.70 g of phenylethyl sulphone were condensed with 0.860 g of valeric aldehyde under the conditions of Example 4. 1.02 g of acetic anhydride were added to the reaction mixture which was then kept for 2 hours at −20°C. 3 g of a colourless oil were obtained, being identified by infrared spectrography as being 2-phenyl sulphonyl-3-acetoxy heptane.

When treated with sodium amalgam under the conditions of the preceding Examples, this product was converted into 2-heptene in a yield of 79 %.

EXAMPLE 6

The procedure is as in Example 5, except that, in the first stage, the acetic anhydride was replaced by 2 g of p-toluene sulphonic acid chloride. After standing overnight at −30°C, the reaction mixture was treated in the usual way, giving 3.9 g of a colourless oil identified by infrared spectrography as being 2-phenyl sulphonyl-3-tosyloxy heptane.

4 g of 6 % sodium amalgam were then added to 760 mg of this product in 6 cc of methanol. The upper decanted layer was found to contain 2-heptene in a quantity corresponding to a yield of 64 %.

EXAMPLE 7

Following the procedure of EXAMPLE 1, 1.70 g of phenylethyl sulphone previously treated with n-butyl lithium in tetrahydrofuran were reacted with 1.26 g of 6-methyl-2-heptenone in 5 cc of the same solvent. After the reaction, the product obtained was treated with a saturated aqueous solution of ammonium chloride, extracted with ethyl ether and then dried over magnesium sulphate. Evaporation of the ether left 2.95 g of an oily product identified by centesimal analysis and chromatography in the vapour phase as being 2-phenyl sulphonyl-3, 7-dimethyl-6-octen-3-ol. The NMR-spectrum of this product revealed the presence of the two diastereo isomers in a ratio of 65 : 35. 655 mg of the alcohol sulphone obtained were contacted overnight at ambient temperature with 3.6 g of 6 % sodium amalgam in 6 cc of absolute ethanol. The mercury and the sodium phenyl sulphinate precipitate were separated: the decanted organic layer was analysed by vapour-phase chromatography. The total yield of 3,7-dimethyl-2,6-octadienes is 52 %, 3,7-dimethyl-6-octen-3-ol having been formed in a quantity corresponding to a yield of 16 %.

If, before being treated with sodium amalgam, the prepared alcohol sulphone is converted into its mesylic ester by reaction with methyl sulphonic acid chloride, 3,7-dimethyl-2,6-octadiene is obtained in a yield of 80 % after reduction with amalgam.

EXAMPLE 8

1.84 g ($10^{-2}$mol) of phenyl isopropyl sulphone in 20 cc of tetrahydrofuran were treated at −78°C with 0.64 g of n-butyl lithium, followed by the addition at −40°C of 0.580 g of acetone in 5cc of tetrahydrofuran. After 1 hour at −30°C, 1.26 g of methyl sulphonic acid chloride were added, followed by the introduction of 4cc of hexemethyl phosphoramide. After standing overnight at −30°C, the reaction mixture was treated in accordance with the preceding Examples, giving 3.2 g of an oily, yellow product identified by centesimal analysis and infrared spectrography as being 2-phenyl sulphonyl-1-mesyloxy-1,1,2,2-tetramethylethane.

Reduction of this product with sodium amalgam under the conditions of the preceding Examples gave tetramethylethylene in a yield of 52 %.

EXAMPLE 9

Reduction of phenylsulphonyl-2-acetoxy-3-dimethyl-3,7-octene-6 of the formula

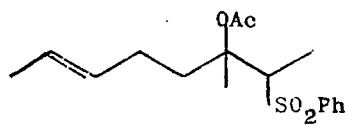

by lithium in ethylenediamine.

338 mg ($10^{-3}$mole) of sulphone acetate and 70 mg ($10^{-2}$mol) of hammer-wrought lithium are stirred at −30° in 9 cm³ of propylamine and 1 cm³ of ethylene diamine.

When the solution becomes blue, 2 cm³ of tertiobutanol, then 10 cm³ of water are added (the protonation is very strong), this mixture is poured into 100 cm³ of iced water, then extracted by 3 times 10 cm³ of pentane, the gathered organic phases are washed with a 15 % NaOH lye then with a brine to neutrality. The pentanic solution is dried on magnesium sulphate then analysed by column gas chromatography.

The yield calculated by internal gauging (undecane) is 28 % of a mixture of cis and trans dimethyl-3,7-octadiene-2,6 of the formulae

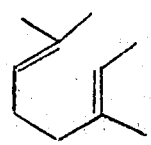   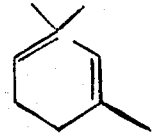

(55)                    (45)

What is claimed is:

1. A process for preparing ethylenic compounds with the formula:

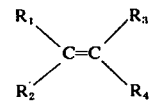

wherein:

$R_1$ and $R_3$ are selected from the group consisting of hydrogen and $CH_3$;

$R_2$ is selected from the group consisting of hydrogen, aromatic hydrocarbon radical, and a saturated or unsaturated, linear or branched aliphatic hydrocarbon;

$R_4$ is selected from the group consisting of phenyl and a saturated or unsaturated linear or branched aliphatic hydrocarbon, where $R_3$ and $R_4$ may be joined to form a ring structure;

which comprises the steps of reacting in the presence of a basic agent selected from the oxides, hydroxides, amides, hydrides and alcoholates of an alkali metal

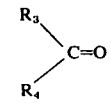 (A)

wherein $R_3$ and $R_4$ are as set forth above and $$R_1-\underset{R_2}{CH}-SO_2R \quad (B)$$

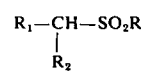

wherein $R_1$ and $R_2$ are as set forth above and R is selected from the group consisting of alkyl, aryl and cycloalkyl to form an alcohol sulphone of the formula:

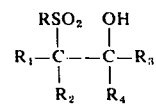 (C)

which sulphone is treated with an alkali metal amalgam reducing agent.

2. The process of claim 1 wherein formula A is selected from the group consisting of acetone, methylethylacetone, methylvinylacetone, 6-methyl-2-heptenone, cyclohexanone, acetophenone, acetaldehyde, propionic aldehyde, valeric aldehyde, benzaldehyde, acrolein, methacrolein, crotonaldehyde, senecioic aldehyde, citral.

3. The process of claim 1 wherein the step of reacting A and B is carried out at a temperature range between ambiant and −80°C.

4. The process of claim 1 wherein the step of reacting A and B is carried out using the basic agent in a ratio of 1 to 1.2 mols per mol of the sulphone (B).

5. The process of claim 1 wherein the first step is carried out in an inert solvent selected from the group consisting of aliphatic hydrocarbon, aromatic hydrocarbons, alcohols, ethers and polar solvents.

6. The process of claim 1, wherein the second step (treating alcohol sulphone) is carried out at a temperature between ambiant and −50°C.

7. The process of claim 1, wherein the second step is carried out with a molar quantity of alkali metal amalgam equal to or greater than that of the alcohol sulphone (C).

8. The process of claim 1, wherein the second step is carried out in an inert solvent selected from the group consisting of aliphatic hydrocarbons, aromatic hydrocarbons, alcohols and linear and cyclic ether.

9. In the (The) process of claim 1, the step wherein the sulphone alcohol (C) is esterified before being subjected to treatment with an alkali metal amalgam reducing agent.

10. The process of claim 9, wherein the sulphone alcohol is esterified by a compound selected from the group consisting of organo sulphonic acids, chloride and anhydride thereof, and carboxylic acids, chloride and anhydride thereof.

11. The process of claim 10, wherein the compound used for esterification is selected from the group consisting of methylsulphonic acid chloride and acetic anhydride p-toluene sulphonic acid chloride.

* * * * *